United States Patent
Maki et al.

(10) Patent No.: US 9,254,108 B2
(45) Date of Patent: Feb. 9, 2016

(54) GANTRY WITH BORE SAFETY MECHANISM

(71) Applicant: General Electric Company, Schenectady, NY (US)

(72) Inventors: Michael Maki, Oconomowoc, WI (US); Brandon Smith, Waukesha, WI (US); Ronald Kulas, Delafield, WI (US); Mark Reznicek, Sussex, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 136 days.

(21) Appl. No.: 14/217,614

(22) Filed: Mar. 18, 2014

(65) Prior Publication Data

US 2015/0265229 A1 Sep. 24, 2015

(51) Int. Cl.
*A61B 6/03* (2006.01)
*H01J 35/18* (2006.01)
*A61B 6/00* (2006.01)
*A61B 6/10* (2006.01)

(52) U.S. Cl.
CPC .................. *A61B 6/035* (2013.01); *A61B 6/032* (2013.01); *A61B 6/10* (2013.01); *A61B 6/4435* (2013.01); *H01J 35/18* (2013.01)

(58) Field of Classification Search
CPC .......... A61B 6/03; A61B 6/032; A61B 6/035; A61B 6/10; A61B 6/102; A61B 6/4429; A61B 6/4435; H01J 35/18
USPC .................. 378/4, 15, 196, 197, 203, 161
See application file for complete search history.

(56) References Cited

U.S. PATENT DOCUMENTS

| | | | | |
|---|---|---|---|---|
| 5,031,198 A * | 7/1991 | Deucher | ............... | A61B 6/035 378/15 |
| 5,703,921 A * | 12/1997 | Fujita | ................... | A61B 6/4488 378/15 |
| 5,761,269 A * | 6/1998 | Sugihara | .............. | A61B 6/4488 378/199 |
| 6,314,157 B1 * | 11/2001 | Tachizaki | ............... | A61B 6/035 378/19 |
| 6,337,894 B1 * | 1/2002 | Tybinkowski | .......... | F16C 33/61 378/15 |
| 6,590,953 B2 * | 7/2003 | Suzuki | ................... | A61B 6/035 310/211 |
| 7,099,427 B2 * | 8/2006 | Cadwalader | .......... | A61B 6/107 250/515.1 |
| 7,108,421 B2 * | 9/2006 | Gregerson | ............. | A61B 6/032 378/146 |
| 7,188,998 B2 * | 3/2007 | Gregerson | ............... | A61B 6/02 378/197 |
| 7,303,334 B2 * | 12/2007 | Cadwalader | ............. | G01D 5/00 378/203 |
| 7,338,207 B2 * | 3/2008 | Gregerson | ............. | A61B 6/032 378/17 |
| 7,384,194 B2 * | 6/2008 | Gatten | ................. | G01N 23/046 378/20 |
| 7,403,596 B1 | 7/2008 | Chaves | | |
| 7,415,094 B2 * | 8/2008 | Johnson | ............... | G01N 23/046 378/208 |
| 7,447,294 B2 * | 11/2008 | Sadotomo | .............. | A61B 6/035 378/15 |

(Continued)

*Primary Examiner* — Allen C. Ho
(74) *Attorney, Agent, or Firm* — Lucas Divine

(57) ABSTRACT

A tomography system may be used to scan a subject and provide reconstructed images of the subject. A gantry of the tomography system has a rotary member that is rotatable around an axis. While the rotary member rotates, a skid layer provides safety features between the rotary member and a subject-facing scan window.

20 Claims, 12 Drawing Sheets

(56) References Cited

U.S. PATENT DOCUMENTS

| | | | |
|---|---|---|---|
| 7,477,721 B2 * | 1/2009 | Chappo | A61B 6/032 378/13 |
| 7,494,275 B2 * | 2/2009 | Buttner | A61B 6/035 378/193 |
| 7,591,590 B2 * | 9/2009 | Cadwalader | G01D 5/00 250/519.1 |
| 7,679,073 B2 * | 3/2010 | Urano | A61N 5/10 250/492.3 |
| 7,755,057 B2 * | 7/2010 | Kim | G01T 1/1611 250/363.09 |
| 8,023,615 B2 | 9/2011 | Fukushima et al. | |
| 8,246,247 B2 * | 8/2012 | Luecke | A61B 6/032 250/363.02 |
| 8,503,616 B2 * | 8/2013 | Chaves | H01J 35/18 378/140 |
| 8,630,696 B2 * | 1/2014 | Kim | A61B 6/032 250/363.03 |
| 8,681,930 B2 * | 3/2014 | Sharpless | A61B 6/035 378/197 |
| 8,903,038 B2 * | 12/2014 | Matsuzawa | A61B 6/035 378/13 |
| 8,917,813 B2 * | 12/2014 | Maurer, Jr. | A61N 5/10 378/197 |
| 9,044,152 B2 * | 6/2015 | Abenaim | G01N 23/046 |
| 9,125,613 B2 * | 9/2015 | Gregerson | A61B 6/4488 |
| 9,198,631 B2 * | 12/2015 | Hara | A61B 6/508 |
| 9,204,850 B2 * | 12/2015 | Smith | A61B 6/44 |
| 2008/0075224 A1 | 3/2008 | Cadwalader et al. | |
| 2009/0141853 A1 * | 6/2009 | Crews | A61B 6/032 378/4 |
| 2010/0074411 A1 | 3/2010 | Chaves | |
| 2011/0077511 A1 | 3/2011 | Kim et al. | |
| 2012/0230465 A1 | 9/2012 | Matsuzawa | |
| 2013/0053676 A1 * | 2/2013 | Kemper | A61B 6/035 600/407 |
| 2013/0158382 A1 * | 6/2013 | Chao | A61N 5/1082 600/407 |

* cited by examiner

GANTRY WITH BORE SAFETY MECHANISM

BACKGROUND

The subject matter disclosed herein relates generally to gantry design and, more particularly, safety mechanisms for gantries.

Gantries are an important part of radiography and tomography systems. A medical imaging system can include a gantry comprising a stationary frame supporting a rotary member about a scanning axis of a scanner. The rotary member includes a central opening large enough to receive a patient extending along the scanning axis. The rotary member is rotated about a patient during a scanning or imaging procedure. An x-ray tube can be positioned on the rotary member diametrically across the central opening from an array of x-ray detectors. As the rotary member rotates, the x-ray tube projects a beam of energy, or x-rays, along a scan plane, through a patient, and to the detector array. By rotating the x-ray source about the scanning axis and relative to the patient, x-rays are projected through a patient from many different directions. An image of the scanned portion of a patient can be constructed from data provided by the detector array using a computer.

As the opening size inside a gantry increases, the amount of space in the gantry for components, materials, and safety mechanisms can be reduced. In addition, as a gantry opening depth gets longer, a patient may start to feel claustrophobic. If a patient, or subject, pushes outward from inside a gantry opening with insufficient safety mechanisms, the force could damage the gantry or injure the patient. Safety mechanisms in gantry design are needed to ensure smooth operation, safety, and fault tolerance.

BRIEF DESCRIPTION

In accordance with an embodiment, a gantry for a tomography system is provided, comprising a stationary structure having a bore extending therethrough; a scan window within the bore, attached to the stationary structure; a rotary member attached to the stationary structure, wherein the rotary member rotates around the bore; and a skid layer between the rotary member and the scan window. The scan window can comprise low-attenuation material.

The skid layer can prevent contact between the scan window and the rotary member. The skid layer can comprise multiple skid pieces. The skid layer may be disposed around the entire circumference or partial circumference of the bore. The skid layer can comprise a plurality of corrugations. The bore-facing surface of the skid layer may be substantially smooth. The skid layer may be attached to the rotary member or the stationary structure.

The gantry can further comprise an x-ray source and an x-ray detector attached to the rotary member; wherein the x-ray source emits x-rays toward a subject and the x-ray detector receives x-rays attenuated by the subject and the scan window. In accordance with an embodiment, the skid layer comprises openings to allow x-rays to pass through un-attenuated to the scan window and x-ray detector. In accordance with an embodiment, the emitted x-rays are partially attenuated by the skid layer.

In accordance with an embodiment, a rotary member is provided comprising a frame to which tomography components may be attached; a bore extending through the center of the frame, wherein the frame rotates around the bore; a skid layer attached to the inner, bore-facing side of the frame; wherein the bore-facing surface of the skid layer is substantially smooth; and wherein the skid layer prevents access to the interior of the frame from the bore. The rotary member can further comprise an x-ray source and an x-ray detector attached to the frame; and wherein the x-ray source emits x-rays toward a subject in the bore and the x-ray detector receives x-rays attenuated by the subject; and wherein the skid layer comprises openings to allow x-rays to pass through un-attenuated to the subject and the x-ray detector.

DETAILED DESCRIPTION

Figure 1:
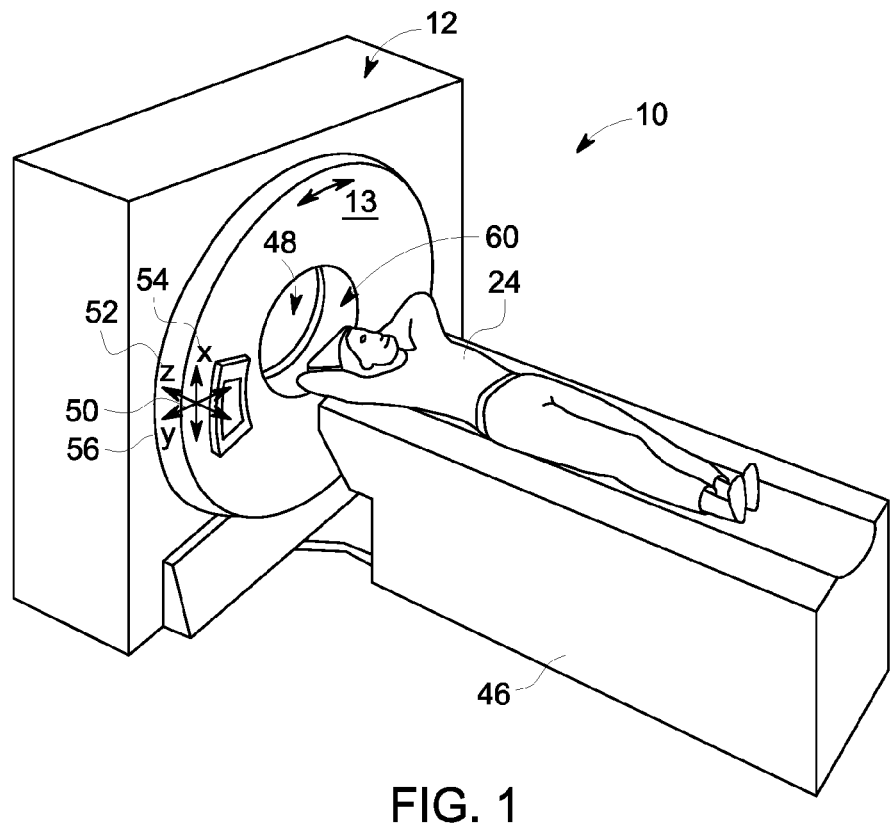
FIG. 1 is a perspective view of a medical imaging system with a gantry in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 2:
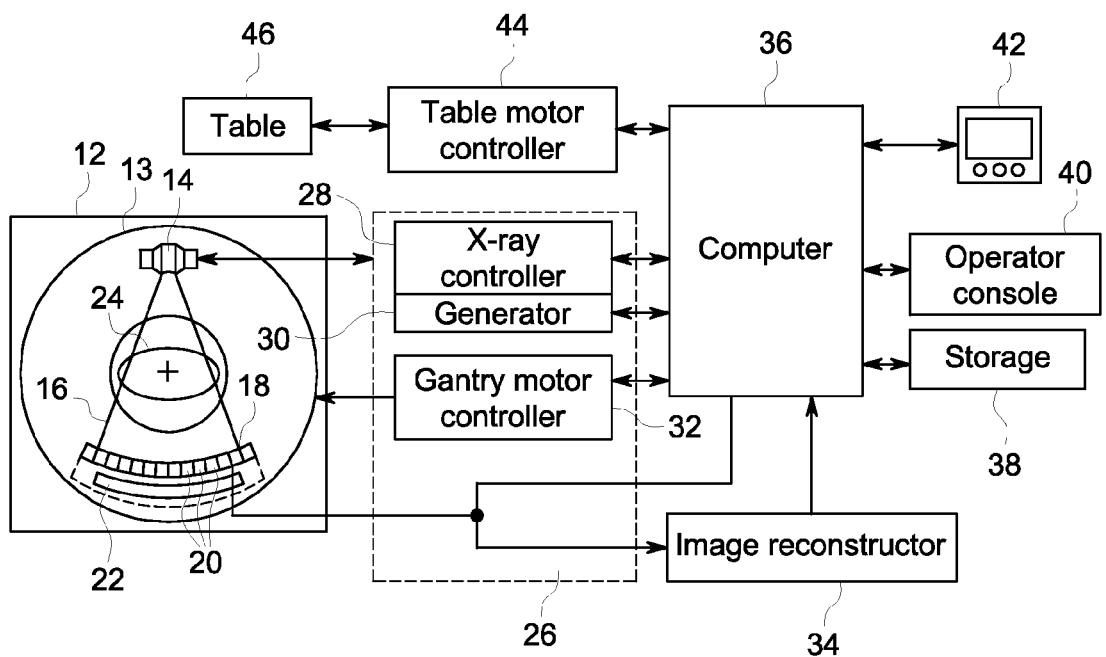
FIG. 2 is a block schematic diagram of a medical imaging system in accordance with an embodiment.

FIGS. 1 and 2 show a computed tomography (CT) imaging system 10 including a gantry 12. Gantry 12 has a rotary member 13 an x-ray source 14 that projects a beam of x-rays 16 toward a detector assembly 18 on the opposite side of the rotary member 13. A main bearing may be utilized to attach the rotary member 13 to the stationary structure of the gantry 12. X-ray source 14 includes either a stationary target or a rotating target. Detector assembly 18 is formed by a plurality of detectors 20 and data acquisition systems (DAS) 22. A collimator can be included at the detector end and/or at the x-ray emission end depending on the particular embodiment configuration. The plurality of detectors 20 sense the projected x-rays 16 that pass through a subject 24, and DAS 22 converts the data to digital signals for subsequent processing. Each detector 20 produces an analog or digital electrical signal that represents the intensity of an impinging x-ray beam 16 and hence the attenuated beam as it passes through subject 24. During a scan to acquire x-ray projection data, rotary member 13 and the components mounted thereon can rotate about a center of rotation.

Rotation of rotary member 13 and the operation of x-ray source 14 are governed by a control mechanism 26 of CT imaging system 10. Control mechanism 26 can include an x-ray controller 28 and generator 30 that provides power and timing signals to x-ray source 14 and a gantry motor controller 32 that controls the rotational speed and position of rotary member 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, motorized table 46 moves a subject 24 through a gantry bore 48, or opening, in whole or in part. A coordinate system 50 defines a patient or Z-axis 52 along which subject 24 is moved in and out of gantry bore 48, a gantry circumferential or X-axis 54 along which detector assembly 18 passes, and a Y-axis 56 that passes along a direction from a focal spot of x-ray tube 14 to detector assembly 18. Scan window 60 lines in the inside of the gantry bore 48 closest to patient 24, discussed further below.

Figure 3:
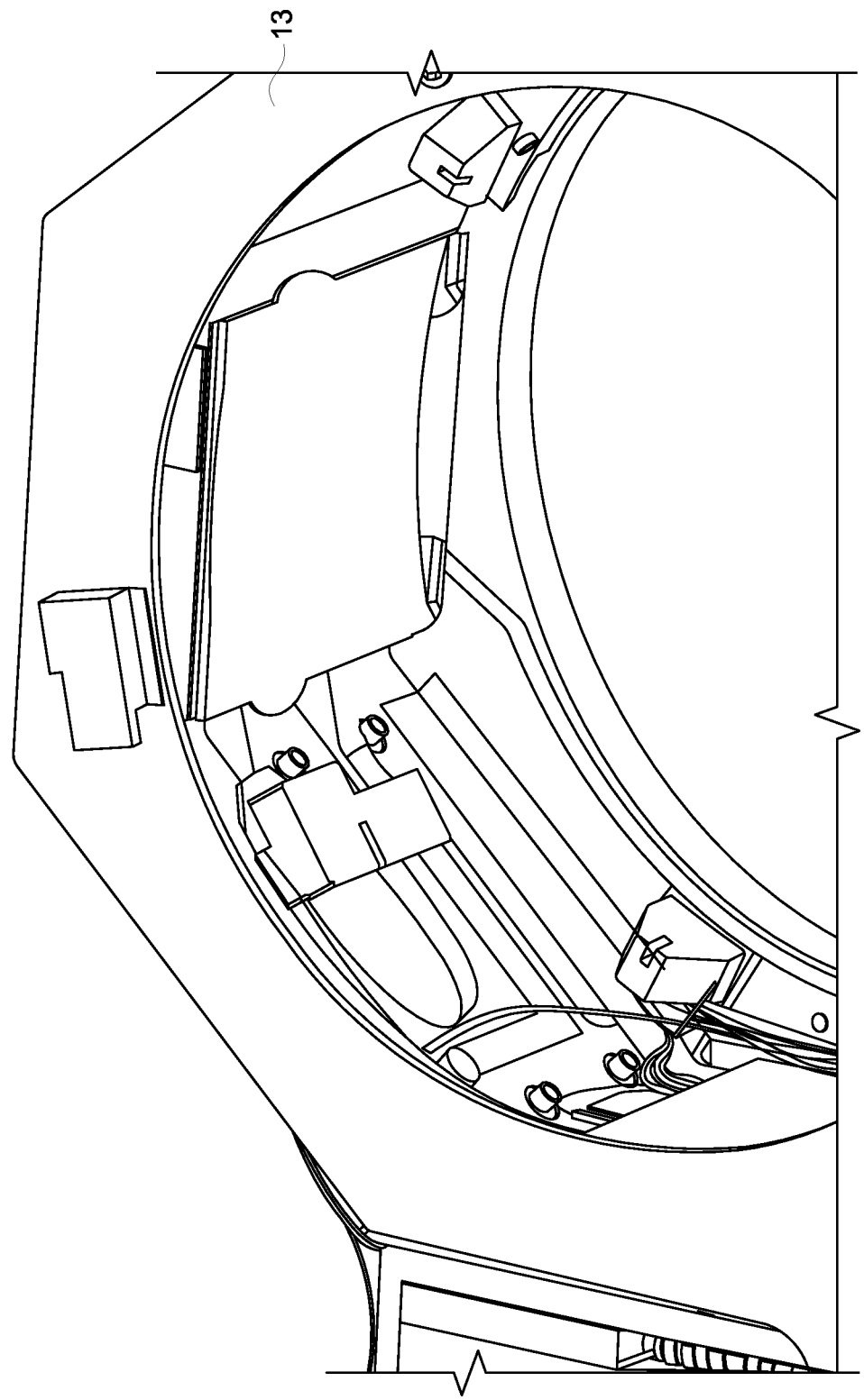
FIG. 3 is a perspective view of a rotary member in accordance with an embodiment.

FIG. 3 is an exemplary view of rotary member 13. Rotary member 13 has various components (such as x-ray source 14, high voltage generator, heat exchanger, collimator, detector assembly 18, circuit board chassis, balance weight, or power supply), electrical cords, and other items attached to its frame. This can create a sharp and irregularly shaped mass that rotates at high speeds around a subject 24 to be scanned.

Figure 4:
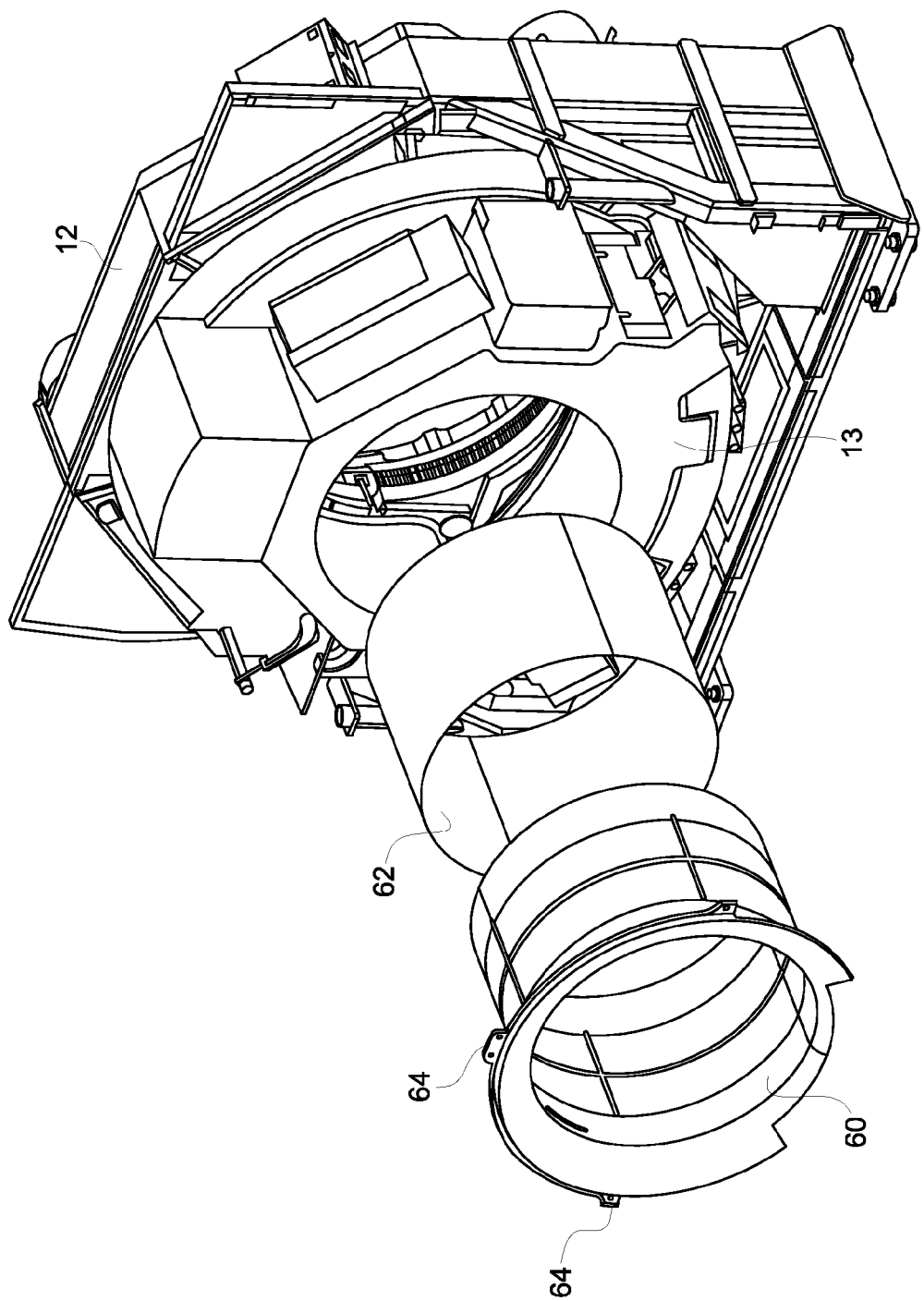
FIG. 4 is a perspective view of a gantry with a scan window and skid layer in accordance with an embodiment.

FIG. 4 is an exemplary view of gantry 12 that includes a rotary member 13, scan window 60, and skid layer 62, according to one embodiment. Gantry 12 includes a stationary structure, or framing, that supports the various items in gantry 12. In this embodiment, gantry 12 is stationary on a floor. Rotary member 13 rotates around the rotation axis where a subject or patient 24 can be in image scanning operations.

Scan window 60 is attached to the stationary structure of gantry 12 in one embodiment. An example of how this can be done is shown as the fastener holes 64 in FIG. 4. Fasteners can be bolts or other fastening materials known in the art. Scan window 60 is the closest physical layer of gantry 12 to the patient or subject during a scan. Scan window 60 is what a patient 24 sees if lying in the gantry bore 48, and thus scan window 60 is accessible to patient 24.

Scan window 60 generally comprises low attenuation material, such as polycarbonate or carbon fiber, in order to maximize the amount of x-rays that pass through the imaged patient or subject 24 to the detector assembly 18. Scan window 60 can be quite thin in some embodiments, from a few millimeters of material to less than a millimeter. The thinner the layer of scan window 60, the less x-ray attenuation likely occurs. The material makeup and thinness of scan window 60 assists in creating high image quality for the final images. Scan window 60 may have transparent sections allowing alignment lasers to function in the CT process. Scan window 60 can also be called a liner, cover, cover assembly, or patient surface.

Skid layer 62 adds a safety mechanism between scan window 60 and rotary member 13, which could have sharp or irregular edges as discussed above in relation to FIG. 3 and FIG. 4. Skid layer 62 prevents contact between scan window 60 and rotary member 13 and any of the items or components attached to rotary member 13. If a patient 24 applies force from the inside of the gantry bore 48 against scan window 60, scan window 60 may bend or deflect towards rotary member 13. Skid layer 62 prevents such bending or deflecting in scan window 60 from coming in contact with irregular shapes on rotary member 13. Further, if any component inside gantry 12 becomes dislodged or any liquid comes loose, skid layer 62 can help protect scan window 60 from any such abnormal operating condition occurring inside gantry 12. Thus, skid layer 62 provides two-way protection. Skid layer 62 helps maximize gantry bore size, especially useful for wide or large bore gantries where scan window 60 is encouraged to be as close to rotary member 13 as possible. Skid layer 62 can also be called a shield, skid plate, skid ring, safety ring, protective ring, protective layer, or bore safety layer.

FIG. 4 shows skid layer 62 as two halves of a tube-like layer according to an embodiment. Skid layer 62 is fastened to, mounted on, or attached to rotary member 13 in certain embodiments. Skid layer 62 rotates around patient 24 and scan window 60 consistent with the movement of rotary member 13. Skid layer 62 can be attached to the stationary gantry in alternative embodiments. Skid layer 62 can have a smooth, or substantially smooth, inner (bore-side, or bore-facing) surface. Skid layer 62 can be made from carbon fiber, aluminum, or other strong and thin metal. Skid layer 62 is can be thin, such as two millimeters or less in one embodiment. Skid layer 62 can have openings, or slots, within it to allow x-ray or laser passage so as to not attenuate or scatter either electromagnetic signal. Alternatively, skid layer 62 may not have such openings, thus partially attenuating the emitted x-rays.

Figure 5:
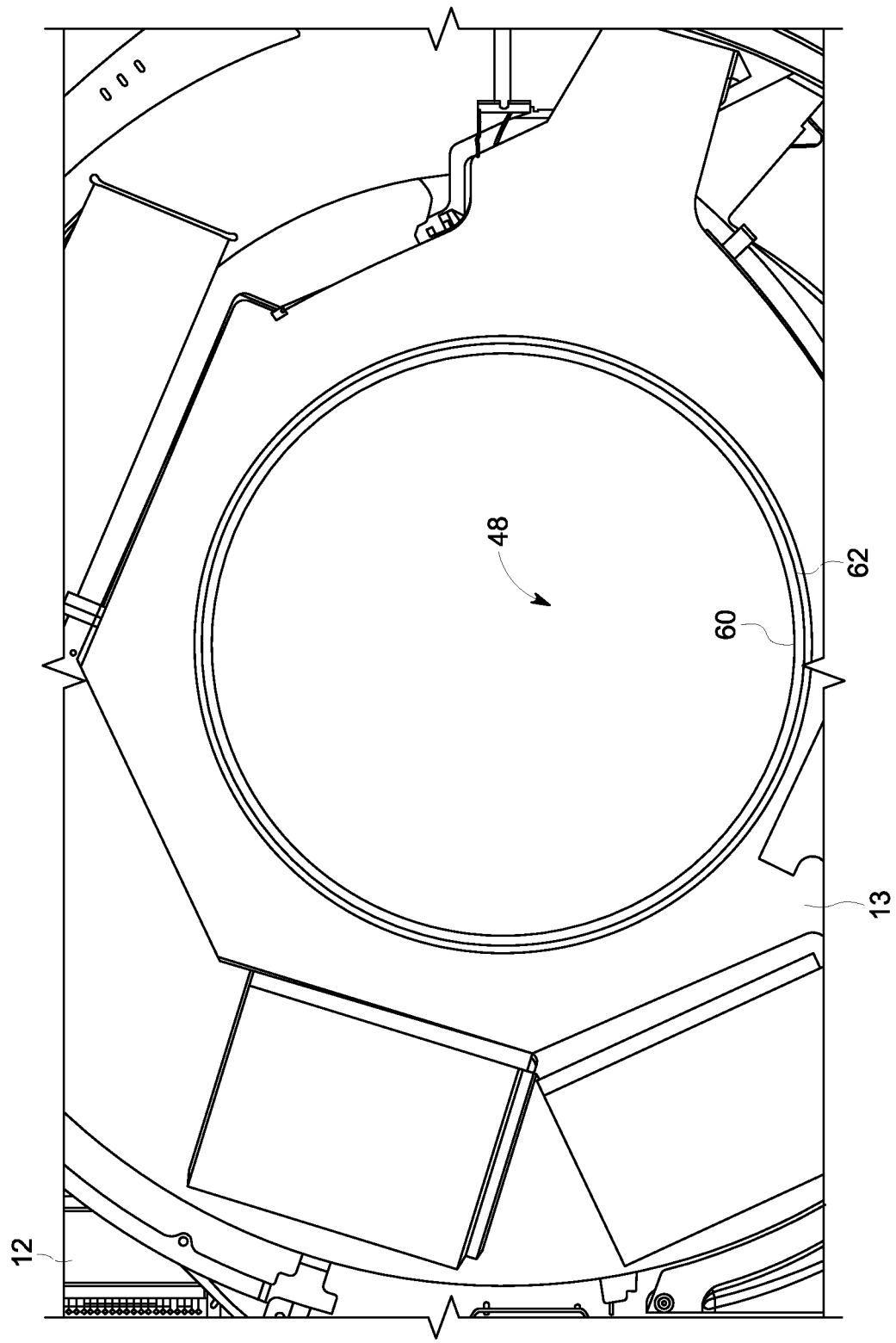
FIG. 5 is a front view of a gantry with a scan window and skid layer in accordance with an embodiment.

FIG. 5 shows a front view of an exemplary gantry 12 according to one embodiment. Gantry 12 includes rotary member 13. Scan window 60 wraps around gantry bore 48 acting as the innermost layer of gantry 12. Skid layer 62 is located between scan window 60 and rotary member 13.

Figure 6:
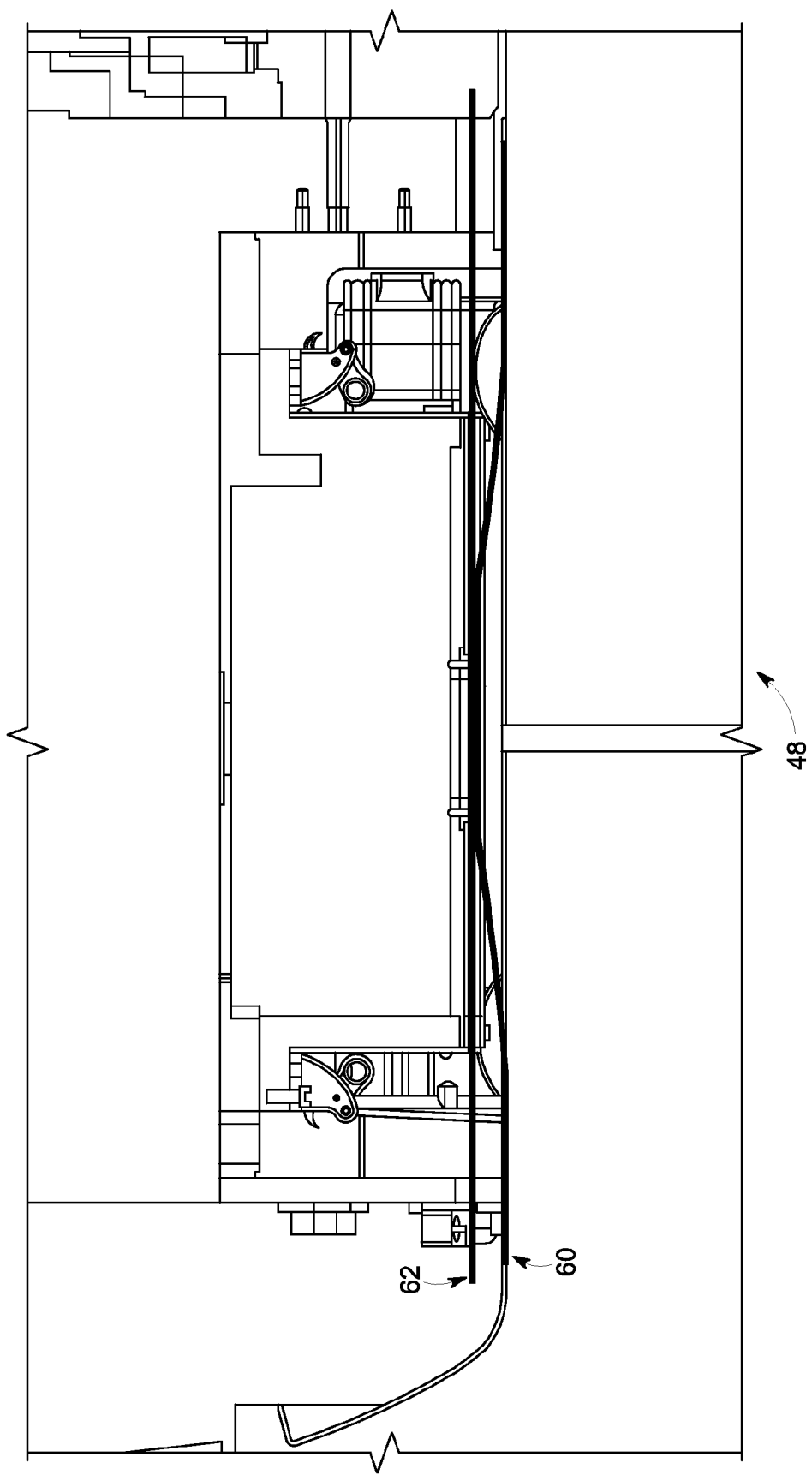
FIG. 6 is a front view of a gantry with applied pressure to the scan window in accordance with an embodiment.

FIG. 6 shows a zoomed, and sectioned side view of the gantry system according to one embodiment. FIG. 6 shows scan window 60 deflecting or bending due to pressure applied upwards. Skid layer 62 acts as a shield between scan window 60 and other gantry components. Further, mounted items within the rotary member 13 or gantry 12 cannot pass by skid layer 62 into scan window 60.

Figure 7:
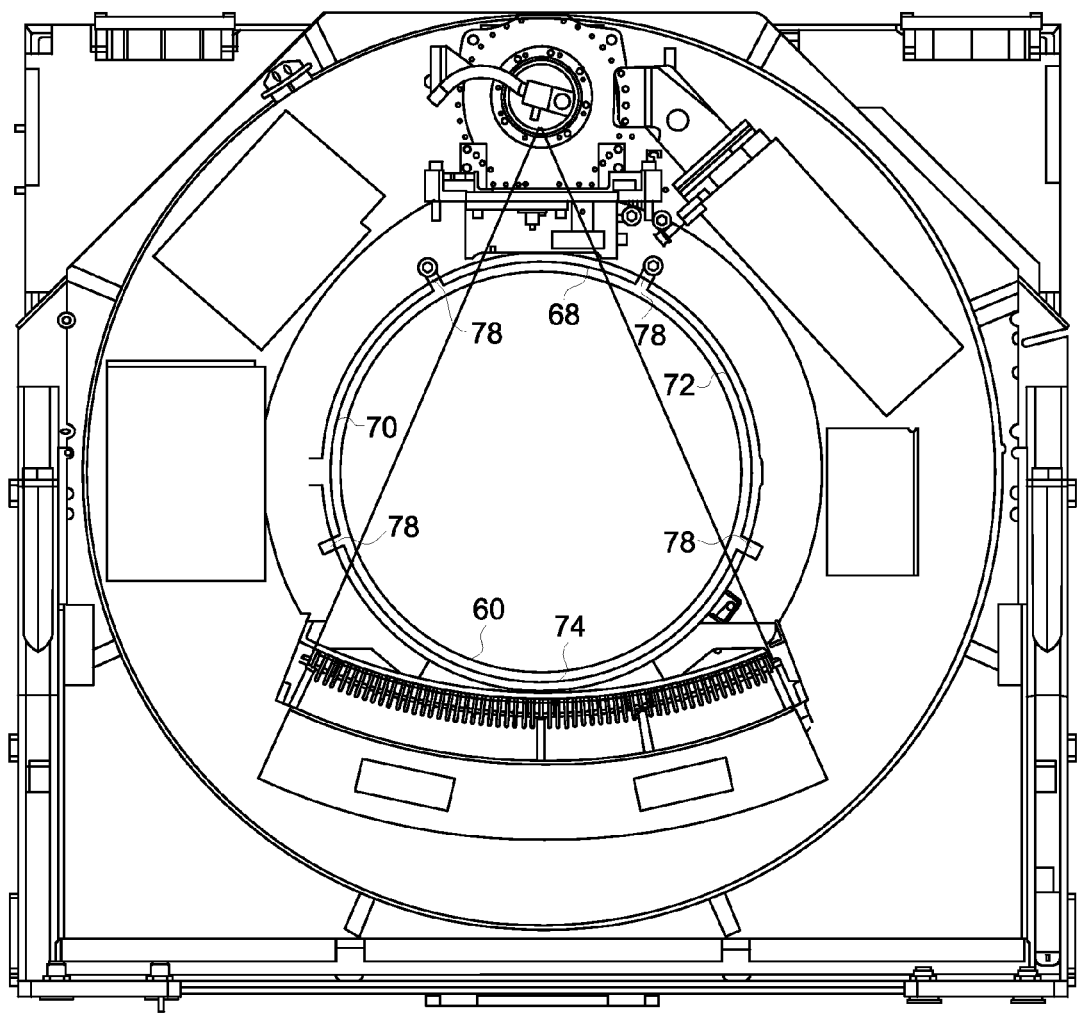
FIG. 7 is a front view of a gantry system with skid pieces in accordance with an embodiment.

FIG. 7 shows a gantry system with a segmented skid layer arrangement according to one embodiment. Skid pieces 68, 70, 72, and 74 combine to function as the skid layer 62 in this embodiment. This arrangement can lead to improved access to gantry sections for service and repair access.

Collimator skid piece 68 is nearest to the x-ray source 14 and collimator in this embodiment. Detector skid piece 74 is nearest to the detector assembly 18. Collimator skid piece 68 and detector skid piece 74 extend past both sides of the x-ray beam 16 in this embodiment to keep a constant attenuation across the beam. Each can be removed during service. Thus, only collimator skid piece 68 needs to be removed for service, for example. The remaining skid pieces 70, 72, and 74 of skid layer 62 would not have to be removed to service the collimator or x-ray source 14. Collimator skid piece 68 and/or detector skid piece 74 can also be removed to lower x-ray attenuation. Left skid piece 70 and right skid piece 72 then rarely have to be removed then in this embodiment. Their constant attachment has the added benefit to provide preserved protection if collimator skid piece 68 or detector skid piece 74 is not re-mounted correctly by a service technician.

Segmentation allows for varied designs in skid pieces. Each skid piece can be specifically tweaked in fabrication to be the highest quality for its function. Thus, skid pieces 68, 70, 72, and 74 do not all need to be of the same materials. For example, collimator skid piece 68 could require cutouts for the x-ray beam 16, shown in FIG. 7, while right skid piece 72 has no x-ray beam passing through and may not require cutouts.

FIG. 7 also shows connection lips 78. Connection lips 78 prevent any liquids or small particles from entering the space between the skid layer 62 and scan window 60. Liquids can be cooling liquids such as oil or water. As this embodiment shows, skid layer 62 can be a single tube (or cylinder), portions of a tube, or segments of a tube positioned strategically around the rotary member 13. Connection lips 78 can be connected to gantry 12 or each other in various ways. Thus, skid pieces 68, 70, 72, and 74 can have small gaps between them or be connected or attached to each other through mechanisms on connection lips 78.

Figure 8A:
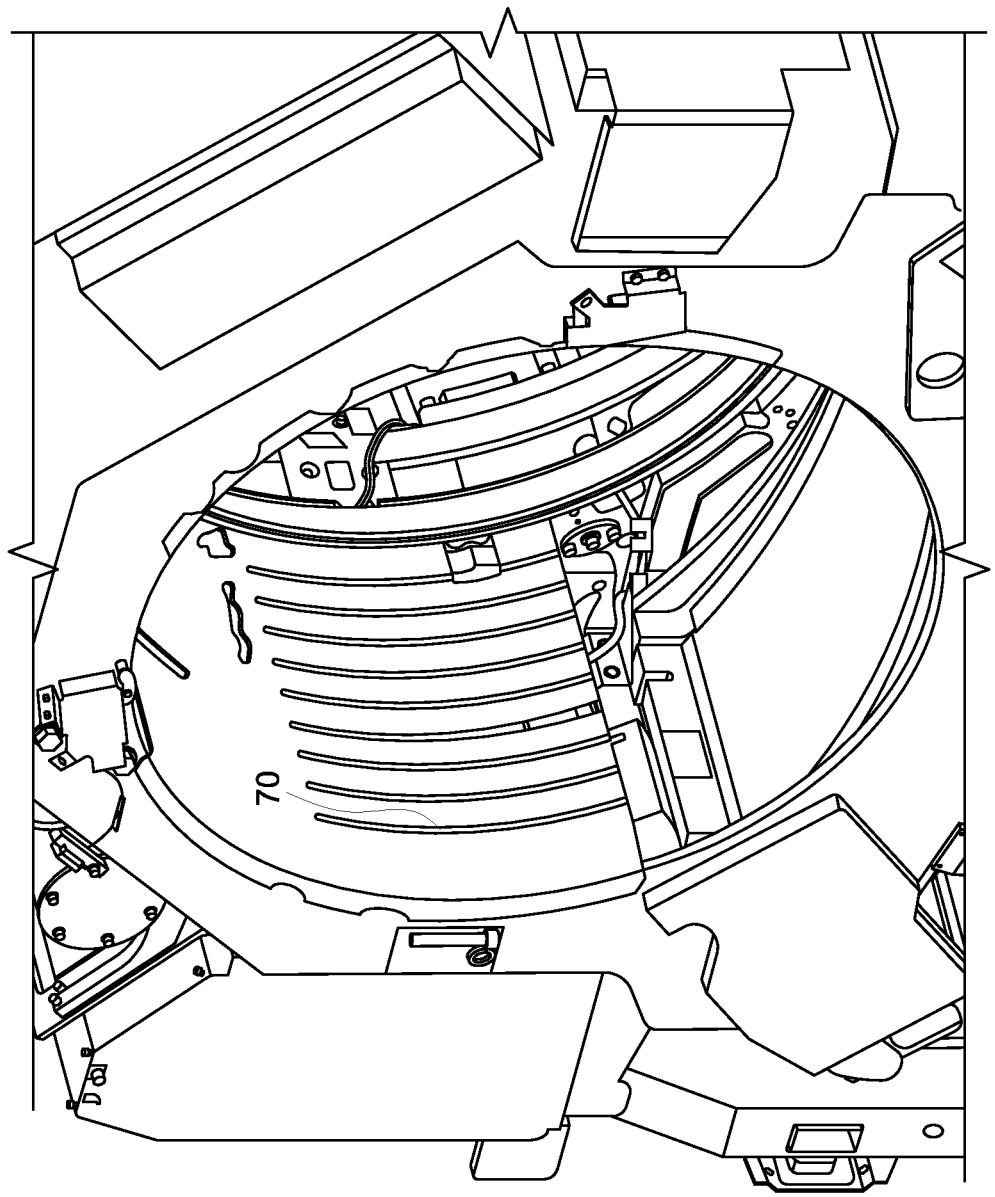
FIG. 8A is a perspective view of a gantry system showing a left skid piece in accordance with an embodiment.
Figure 8B:
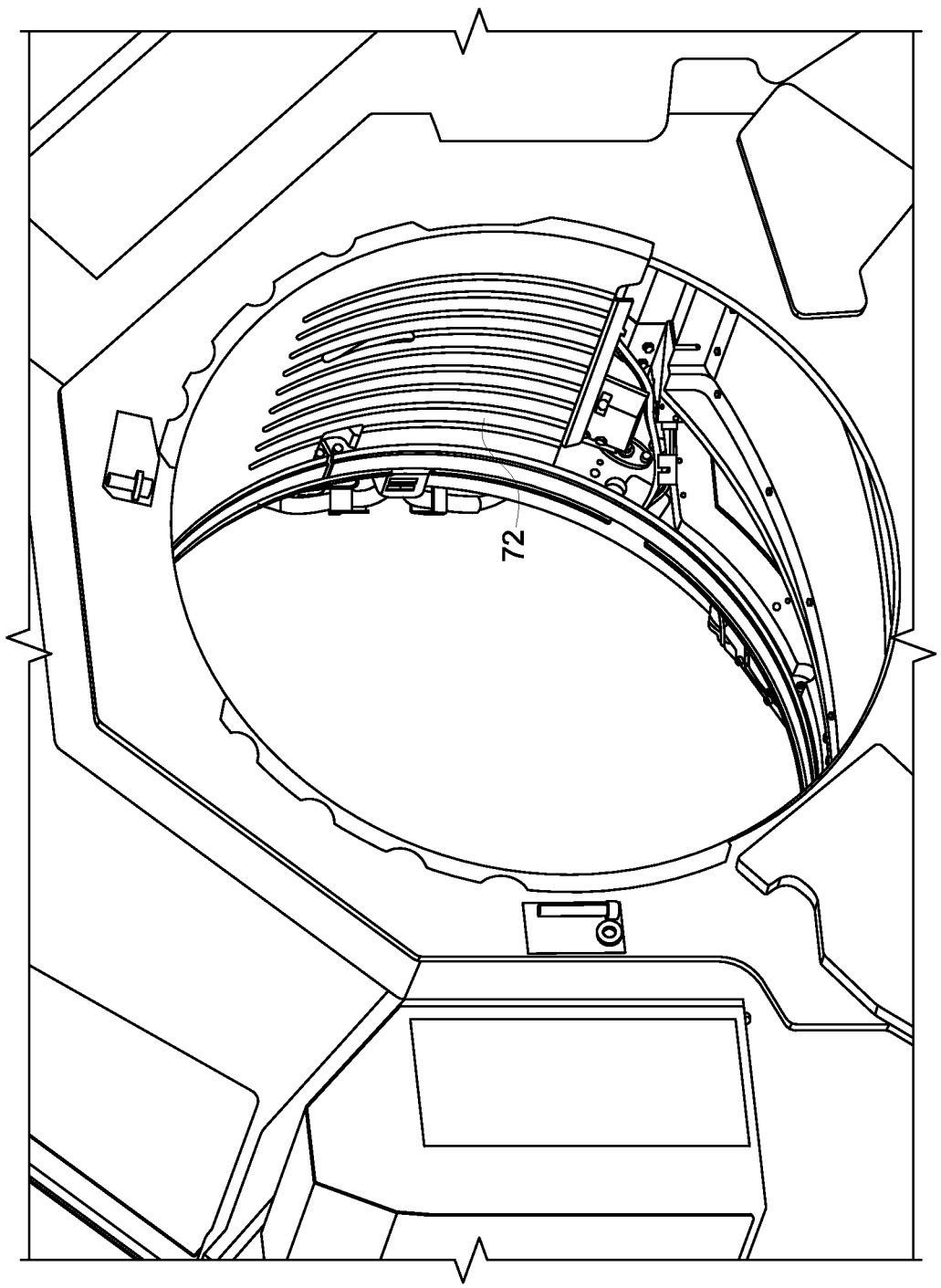
FIG. 8B is a perspective view of a gantry system showing a right skid piece in accordance with an embodiment.

FIGS. 8A and 8B show perspective views of the gantry system according to an embodiment. FIG. 8A shows left skid piece 70 attached to the rotary member 13 on the left side of the gantry bore 48. Scan window 60 is not shown in FIGS. 8A and 8B. FIG. 8B shows right skid piece 72 attached to the rotary member 13 on the right side of the gantry bore 48. Left skid piece 70 and right skid piece 72 make up the entire skid layer 62 in this embodiment. The edges of the skid pieces 70 and 72 may have ramps so as to soften the transition for the scan window 60 between unsupported and supported sections around the circumference of the gantry bore 48. No skid piece is placed over the detector assembly 18 in this exemplary embodiment. A detector skid piece 74 may not be needed in this circumstance because the detector assembly 18 is set so low in the system, it is far enough away from an installed scan window 60 that even a maximum scan window deflection would not cause contact.

Figure 9:
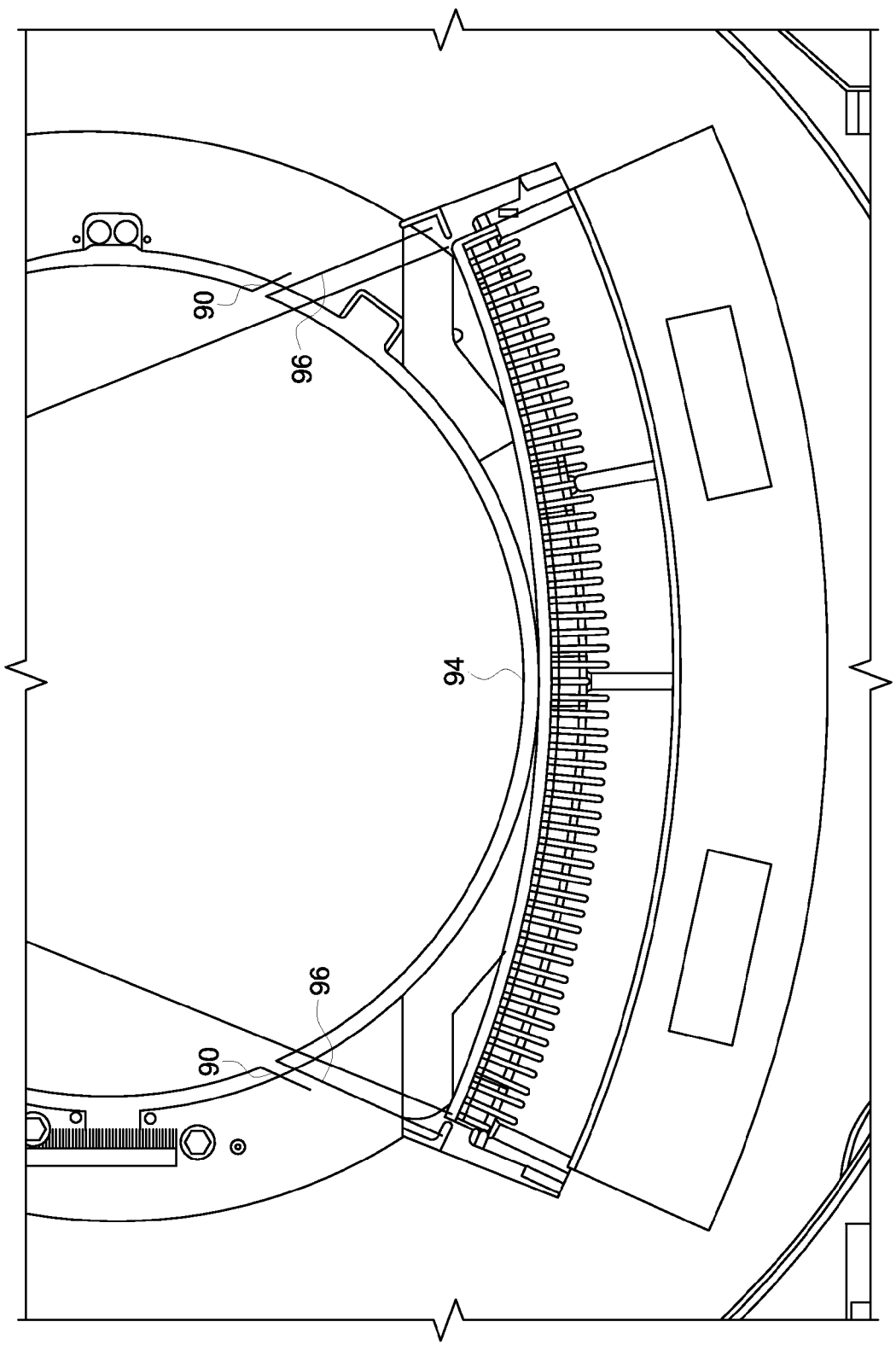
FIG. 9 is a front view of the safety mechanisms on the detector side of the rotary member in accordance with an embodiment.

FIG. 9 shows an alternative embodiment for implementing connection lips. Side skid pieces each have folding lip 90 in this embodiment. Detector skid piece 94 has extending folded lips 96.

Figure 10:
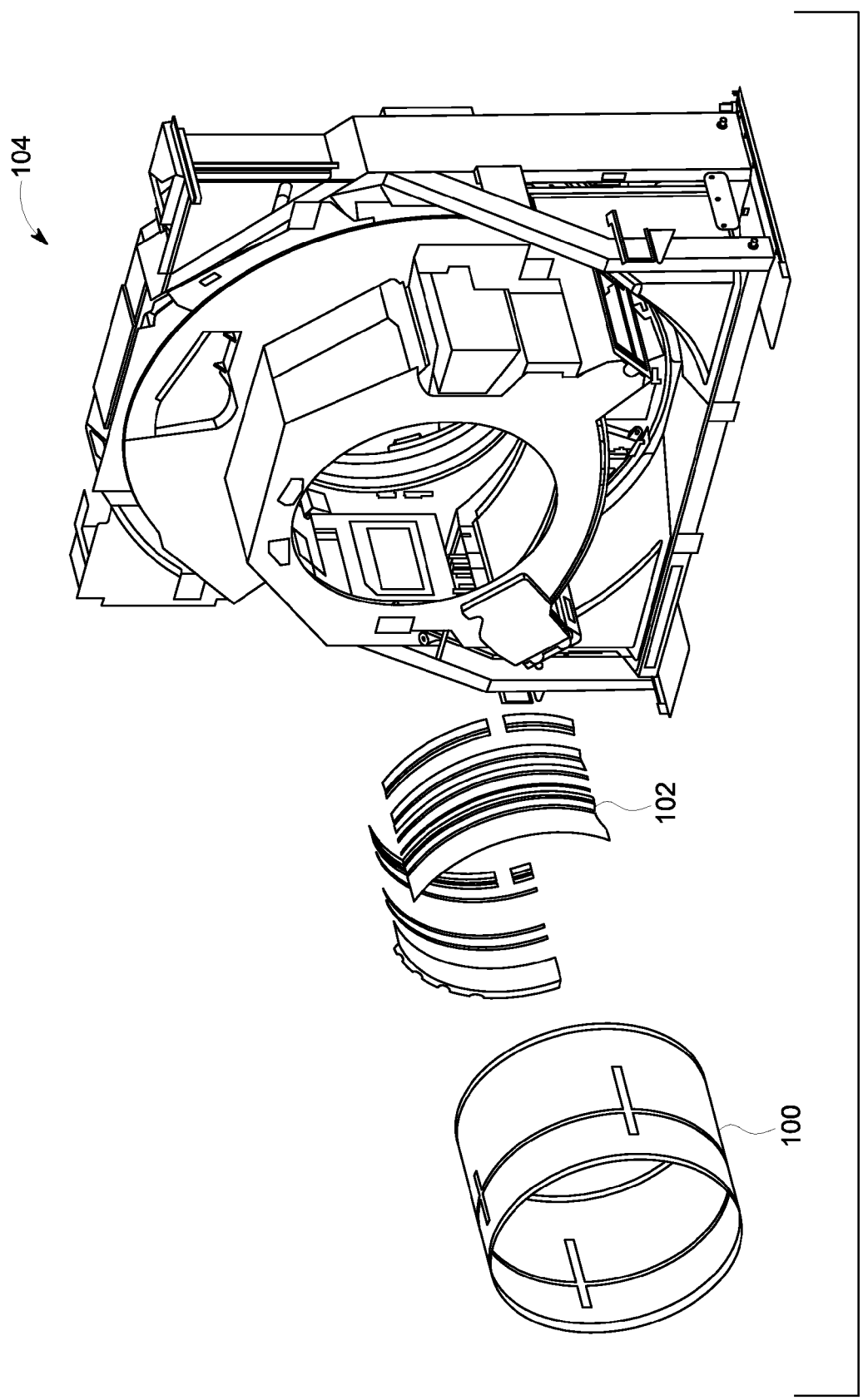
FIG. 10 is a perspective view of a gantry with a scan window and skid layer in accordance with an embodiment.

FIG. 10 shows a perspective view of a gantry system 104 with scan window 100 and skid layer 102, according to one embodiment. Scan window 100 has transparent sections to allow for x-rays, or laser pass-through to allow normal operation of a gantry alignment system. Skid layer 102 is shown as a collection of smaller skid pieces that transverse only a partial circumference of the rotary member 13. Skid layer 102 is shown in FIG. 10 without pieces that cover the x-ray source 14 and detector assembly 18. According to an alternative embodiment, skid pieces covering these sections can be added as well. According to alternative embodiment, the skid pieces shown in FIG. 9 can wrap around the full circumference of the rotary member 13.

Figure 11:
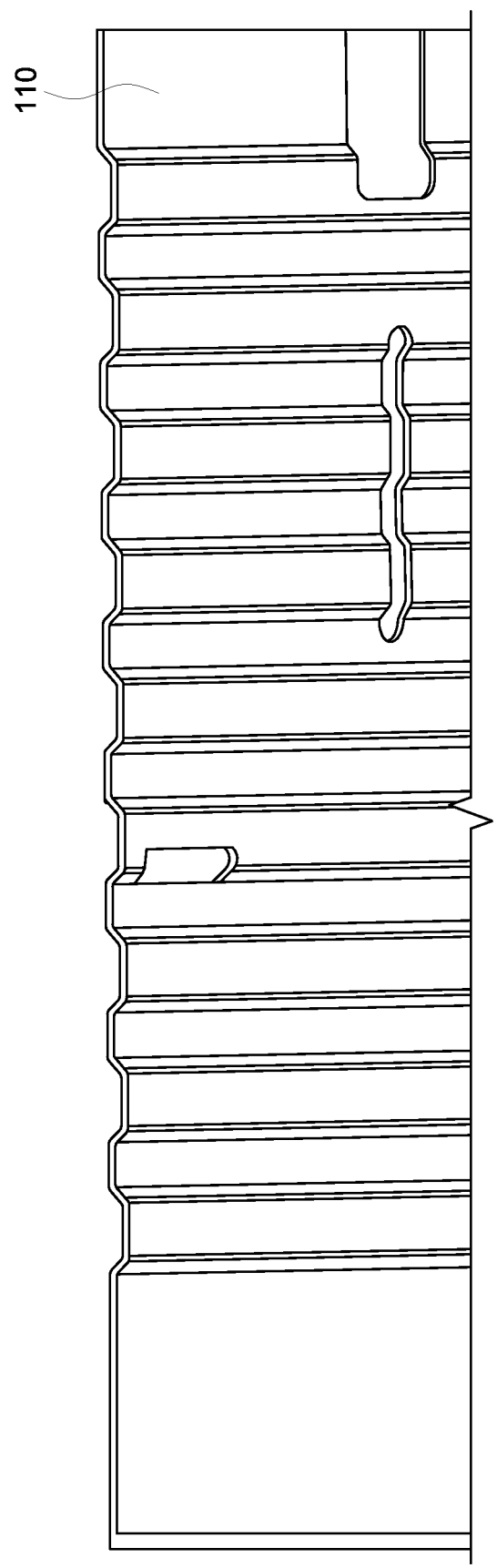
FIG. 11 is a view of a skid layer section in accordance with an embodiment.

FIG. 11 shows skid layer 110 that includes folded or washboard corrugations, according to one embodiment. Such a forming of the material of skid layer 110 can add strength and durability to such a safety system, helping it to withstand the high centrifugal forces during rotation and direct forces from patient impact. Holes in the skid layer 110 can provide pass-through for x-rays and laser alignment lights. Other methods of forming the metal of the skid plate for strengthening may be used.

Figure 12:
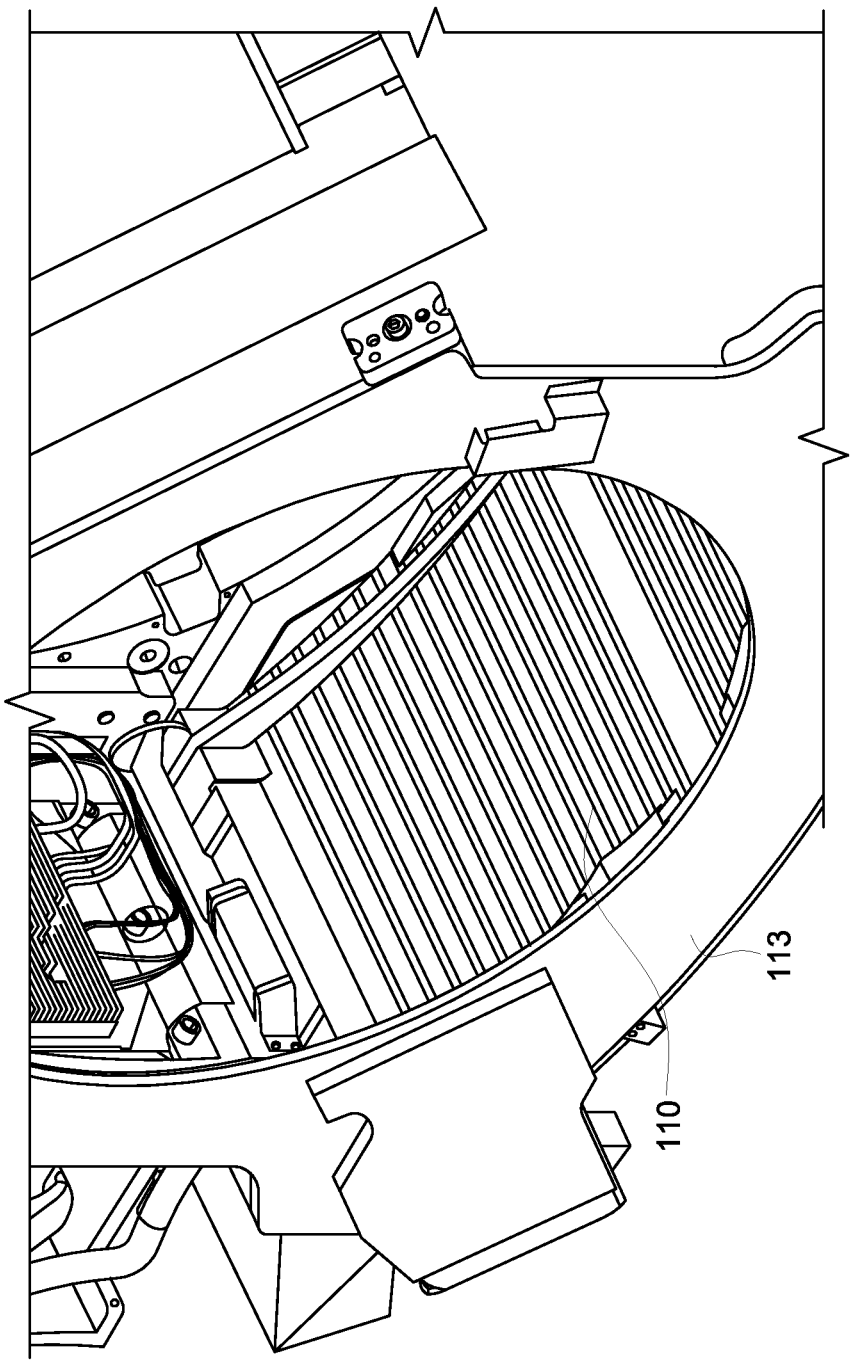
FIG. 12 is a perspective view of a skid layer and rotary member in accordance with an embodiment.

FIG. 12 shows a gantry system including skid layer 110 according to one embodiment. Rotary member 113 has corrugated skid layer 110 installed for safety.

The gantry system shown throughout adds passive, structural safety for the system, components and wires in the system, and an imaged patient. The safety structure does not require electronic switches or other sensory devices to provide the safety. The safety structure does not affect the scan by providing pass-through or a consistent density within the scan beam.

The skid layer may further be used for the attenuation or full blockage of scatter x-rays according to some embodiments. These types of x-rays have no medical benefit and reducing them improves patient health and safety as well as image quality. Thus, the skid layer can allow pass-through of the main x-ray beam for imaging and prevent unwanted scatter x-rays.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A gantry, comprising:
   a stationary structure having a bore extending therethrough;
   a scan window within the bore, attached to the stationary structure;
   a rotary member attached to the stationary structure, wherein the rotary member rotates around the bore; and
   a skid layer between the rotary member and the scan window.

2. The gantry of claim 1, wherein the skid layer is attached to the rotary member.

3. The gantry of claim 1, wherein the skid layer is attached to the stationary structure.

4. The gantry of claim 1, wherein the skid layer prevents contact between the scan window and the rotary member.

5. The gantry of claim 1, wherein the scan window comprises low-attenuation material.

6. The gantry of claim 5, wherein the low-attenuation material is polycarbonate.

7. The gantry of claim 1, wherein the skid layer comprises carbon fiber or aluminum.

8. The gantry of claim 1, further comprising:
   an x-ray source and an x-ray detector attached to the rotary member; and
   wherein the x-ray source emits x-rays toward a subject and the x-ray detector receives x-rays attenuated by the subject and the scan window.

9. The gantry of claim 8, wherein the skid layer comprises openings to allow x-rays to pass through un-attenuated to the scan window and the x-ray detector.

10. The gantry of claim 8, wherein the emitted x-rays are partially attenuated by the skid layer.

11. The gantry of claim 1, wherein the skid layer is disposed around the entire circumference of the bore.

12. The gantry of claim 1, wherein the skid layer is disposed around a partial circumference of the bore.

13. The gantry of claim 1, wherein the skid layer further comprises a plurality of corrugations.

14. The gantry of claim 1, wherein the bore-facing surface of the skid layer is substantially smooth.

15. The gantry of claim 1, wherein the skid layer comprises multiple skid pieces.

16. A rotary member, comprising:
    a frame to which tomography components may be attached;
    a bore extending through the center of the frame, wherein the frame rotates around the bore;
    a skid layer attached to the inner, bore-facing side of the frame;
    wherein the bore-facing surface of the skid layer is substantially smooth; and
    wherein the skid layer prevents access to the interior of the frame from the bore.

17. The rotary member of claim 16, wherein the skid layer comprises multiple skid pieces.

18. The rotary member of claim 16, wherein the skid layer is disposed around the entire circumference of the bore.

19. The rotary member of claim 16, wherein the skid layer is disposed around a partial circumference of the bore.

20. The rotary member of claim 16, further comprising:
    an x-ray source and an x-ray detector attached to the frame; and
    wherein the x-ray source emits x-rays toward a subject in the bore and the x-ray detector receives x-rays attenuated by the subject; and
    wherein the skid layer comprises openings to allow x-rays to pass through un-attenuated to the subject and the x-ray detector.

* * * * *